(12) United States Patent
Evans et al.

(10) Patent No.: US 6,717,001 B2
(45) Date of Patent: *Apr. 6, 2004

(54) PROCESS FOR OPERATING THE EPOXIDATION OF ETHYLENE

(75) Inventors: Wayne Errol Evans, Richmond, TX (US); Peter Ingraham Chipman, Houston, TX (US)

(73) Assignee: Shell Oil Company, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/297,522

(22) PCT Filed: Jun. 5, 2001

(86) PCT No.: PCT/US01/18097

§ 371 (c)(1),
(2), (4) Date: Dec. 6, 2002

(87) PCT Pub. No.: WO01/96324

PCT Pub. Date: Dec. 20, 2001

(65) Prior Publication Data

US 2003/0139633 A1 Jul. 24, 2003

(51) Int. Cl.⁷ .............................................. C07D 301/10
(52) U.S. Cl. ........................ 549/536; 549/534; 568/858
(58) Field of Search ................................ 549/534, 536; 568/858

(56) References Cited

U.S. PATENT DOCUMENTS

| 3,935,279 A | 1/1976 | Cocuzza et al. | |
| 3,960,775 A | 6/1976 | Piccinini et al. | 252/463 |
| 4,400,559 A | 8/1983 | Bhise | |
| 5,011,807 A | 4/1991 | Hayden et al. | 502/218 |
| 5,099,041 A | 3/1992 | Hayden et al. | 549/536 |
| 5,177,225 A | 1/1993 | Ramachandran et al. | 549/534 |
| 5,262,551 A | 11/1993 | Horrell, Jr. et al. | 549/534 |
| 5,380,697 A | 1/1995 | Matusz et al. | |
| 5,545,603 A | 8/1996 | Kemp | |
| 6,372,925 B1 * | 4/2002 | Evans et al. | 549/536 |

FOREIGN PATENT DOCUMENTS

| DE | 198 43 697 A1 | 3/2000 | C07C/29/80 |
| EP | 0 266 015 A1 | 5/1988 | B01J/23/68 |
| EP | 0 557 833 A1 | 2/1992 | C07D/301/10 |
| EP | 0 567 273 A1 | 10/1993 | C07D/301/10 |
| EP | 0 625 370 A1 | 11/1994 | B01J/23/68 |
| GB | 1191983 | 5/1970 | |
| GB | 1319004 | 5/1973 | C07D/1/14 |

* cited by examiner

Primary Examiner—Ba K. Trinh

(57) ABSTRACT

A process for the vapor phase oxidation of ethylene to ethylene oxide, which process involves reacting a reaction mixture having ethylene and oxygen in the presence of a supported highly selective silver-based catalyst by: operating at an initial operation phase wherein fresh catalyst is used, and operating at a further operation phase when a cumulative ethylene oxide production exceeds 0.01 kT ethylene oxide per m3 of catalyst, wherein in said further operation phase the concentration of ethylene in the reaction mixture is increased; and
a method of using ethylene oxide into the 1.2-ethanediol or the 1,2-ethanediol ether wherein the ethylene oxide has been obtained by the process for the production of ethylene oxide.

17 Claims, 2 Drawing Sheets

PROCESS FOR OPERATING THE EPOXIDATION OF ETHYLENE

This application is a 371 of PCT/US01/18097 filed May 6, 2001.

FIELD OF THE INVENTION

The present invention relates to a process for operating the vapor phase epoxidation of ethylene in the presence of a supported highly selective silver based catalyst.

BACKGROUND OF THE INVENTION

In the catalytic epoxidation of ethylene, modern silver-based supported catalysts are highly selective towards ethylene oxide production. Under certain operation conditions their selectivity towards ethylene oxide, expressed as a percentage of the ethylene converted, can reach values above the 6/7 or 85.7 mol % limit which formerly—based on the reaction formula 7 $C_2H_4$+6 $O_2$→6 $C_2H_4O$+2 $CO_2$+2 $H_2O$, see Kirk-Othmer's *Encyclopedia of Chemical Technology*, 3$^{rd}$ ed. vol 9 (1980) p. 445—was considered to be the theoretically maximal selectivity of this reaction. Such highly selective catalysts, which may comprise as their active components silver, rhenium, at least one further metal and optionally a rhenium co-promoter, are disclosed in EP-B-266015 and in several subsequent patent publications.

Like all catalysts, the highly selective silver based ethylene epoxidation catalysts are subject to aging-related performance decline during normal operation and they need to be exchanged periodically. The aging manifests itself by a reduction in both selectivity and activity performance of the catalyst. Selectivity and activity are the primary (although not the only) determinants of plant profitability. There exists, therefore, a considerable economic incentive for delaying the need for exchanging the catalyst by preserving these values as long as possible. Several patent publications are known which are directed at stabilizing the catalyst by introducing modifications in the catalyst composition or in the support material, but thus far the reaction conditions and, in particular, the feed composition escaped attention in this respect.

It is known, for example from EP-A-567273, that when a fresh catalyst is used, operating at a higher concentration of ethylene and/or of oxygen in the reactor feed gas can lead to both a better activity and selectivity of the ethylene epoxidation reaction.

It has now surprisingly been found that aged ethylene oxidation catalysts react differently to the composition of the reactant gas mixture than do fresh ethylene oxidation catalysts, and that in this respect also highly selective catalysts differ from traditional catalysts. More specifically, when with the fresh highly selective catalysts the selectivity of the reaction towards ethylene oxide is not influenced substantially by employing a higher concentration of ethylene, with the aged highly selective catalysts the selectivity is substantially improved. Differences of activity performance under the same conditions of increased ethylene concentration between fresh and aged highly selective catalysts are in the same direction. By contrast to the highly selective catalysts, it has been found that aged and fresh traditional ethylene oxidation catalysts do not exhibit this difference in their reaction to the composition of the feed gas mixture.

SUMMARY OF THE INVENTION

The present invention therefore provides a process for the vapor phase oxidation of ethylene to ethylene oxide, which process comprises reacting a reaction mixture comprising ethylene and oxygen in the presence of a supported highly selective silver-based catalyst by:

operating at an initial operation phase wherein fresh catalyst is used, and operating at a further operation phase when a cumulative ethylene oxide production exceeds 0.01 kT ethylene oxide per m$^3$ of catalyst, wherein in said further operation phase the concentration of ethylene in the reaction mixture is increased.

In preferred embodiments, the invention provides a process for the vapor phase oxidation of ethylene to ethylene oxide in the presence of a supported highly selective silver-based catalyst, at a work rate w in the range of from 32 to 320 kg ethylene oxide produced per m$^3$ of catalyst per hour, the reaction mixture containing ethylene, oxygen, optional carbon dioxide, gas phase moderator and balance inert gases, the reaction temperature being from 180 to 325° C., the reactor inlet pressure from 1000 to 3500 kPa and the GHSV from 1500 to 10000, the process comprising:

operating at an initial operation phase wherein fresh catalyst is used, the reaction gas mixture containing an ethylene concentration which represents an economically optimized balance between catalyst performance (expressed, at the given work rate w, by the selectivity S in mol % and by the operating temperature T in ° C.) on the one hand and ethylene vent losses on the other, and an oxygen concentration which complies with safety-related flammability restrictions; and operating at a further operation phase when the catalyst has reached an advanced aged defined by a cumulative ethylene oxide production exceeding 0.5 kT ethylene oxide per m$^3$ of catalyst, in particular 1.5 kT ethylene oxide per m$^3$ of catalyst, wherein in said further operation phase the composition of the reaction mixture is changed to contain from 1.1 to 4 times the concentration of ethylene used in the initial operation phase and the corresponding optimized and safe concentration of oxygen.

In further preferred embodiments, the invention provides a process for the vapor phase oxidation of ethylene to ethylene oxide in the presence of a supported highly selective silver-based catalyst, at a work rate w in the range of from 32 to 320 kg ethylene oxide produced per m$^3$ of catalyst per hour, the reaction mixture containing ethylene, oxygen, optional carbon dioxide, gas phase moderator and balance inert gases, the reaction temperature being from 180 to 325° C., the reactor inlet pressure from 1000 to 3500 kPa and the GHSV from 1500 to 10000, the process comprising:

operating at an initial operation phase wherein fresh catalyst is used, the reaction gas mixture containing an ethylene concentration which represents an economically optimized balance between catalyst performance (expressed, at the given work rate w, by the selectivity S in mol % and by the operating temperature T in ° C.) on the one hand and ethylene vent losses on the other, and an oxygen concentration which complies with safety-related flammability restrictions; and operating at a further operation phase when the catalyst has aged sufficiently to cause the selectivity S to be reduced by at least 2.5 mol % and/or the activity parameter T to be raised by at least 15° C., wherein the selectivity S and the activity parameter T are as defined hereinafter, and wherein in said further operation phase the composition of the reaction mixture is changed to contain from 1.1 to 4 times the concentration of ethylene used in the initial operation phase and the corresponding optimized and safe concentration of oxygen.

DETAILED DESCRIPTION OF THE INVENTION

Figure 1:
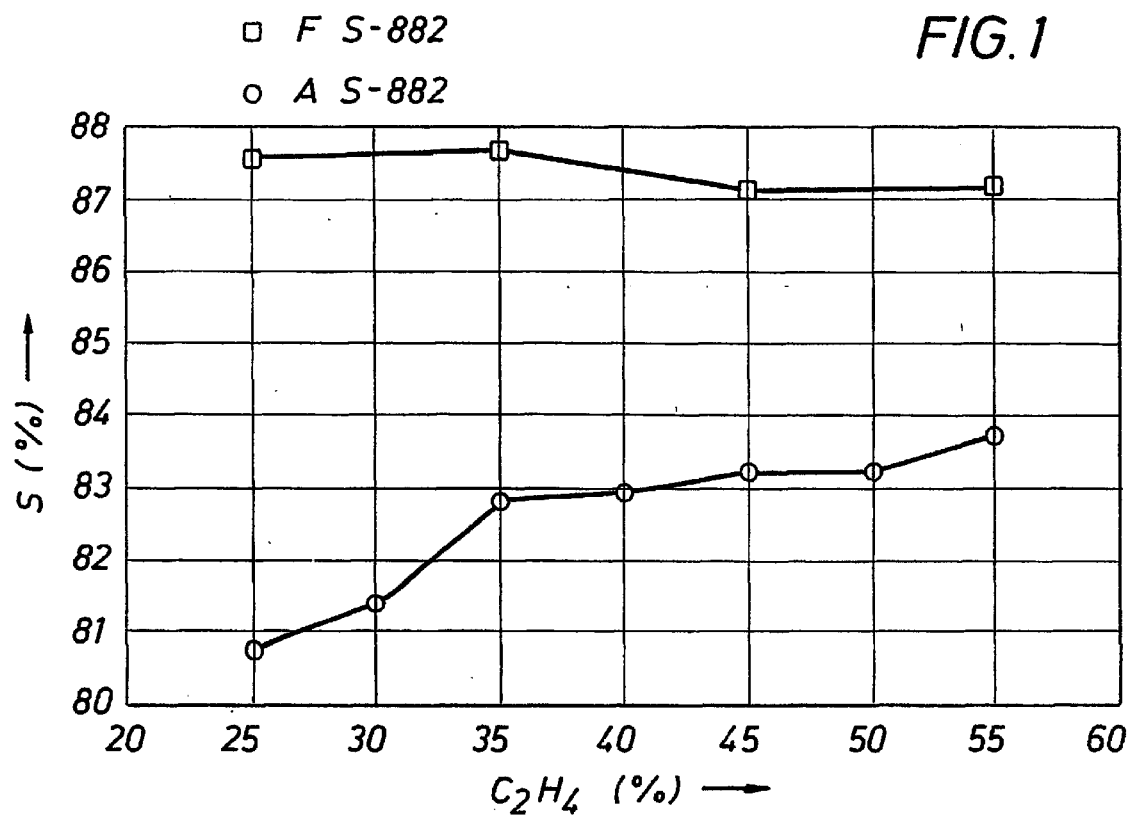
FIG. 1 shows for a fresh high selectivity catalyst ("F S-882") and an aged high selectivity catalyst ("A S-882") the selectivity ("S") versus the ethylene concentration ("$C_2H_4$, %") in the gas feed.

As used herein, "aged catalyst" means a catalyst which, in the course of operation, has reached an advanced age defined by a cumulative ethylene oxide production exceeding 0.01 kT ethylene oxide per $m^3$ of catalyst, and "fresh catalyst" means a catalyst immediately after its preparation or rejuvenation, or a catalyst which, in the course of operation, has not yet reached the advanced age as defined. Frequently, the aged catalyst has aged sufficiently to cause the selectivity S to be reduced by at least 2.5 mol % and/or the activity parameter T to be raised by at least 15° C., wherein the selectivity S and the activity parameter T are as defined hereinafter.

The vapor phase (direct) oxidation processes of ethylene to ethylene oxide can be air-based or oxygen-based, see Kirk-Othmer's *Encyclopedia of Chemical Technology*, 3rd ed. vol 9 (1980) p. 445–447. In the air-based processes air or air enriched with oxygen is fed directly to the system while in the oxygen-based processes high-purity (>95 mol %) oxygen is employed as the source of the oxidizing agent. Presently most ethylene oxide production plants are oxygen-based and this is the preferred embodiment of the present invention.

Both air-based and oxygen-based processes require the venting of a purge stream in order to avoid accumulation of inert gases, though the purge stream of the air-based process is much larger because of the large amount of nitrogen which is constantly introduced. In any case, at least some ethylene is always lost with the purge stream. The amount of ethylene lost in this way depends on the purge stream (which as indicated above is smaller in oxygen-based plants) but also on the concentration of ethylene in the reaction gas mixture. The technical and economical conditions (including the price of ethylene) determine for every individual plant an optimized balance between best catalyst performance and least ethylene vent losses.

Further, in order to remain outside the flammability limit of the gas mixture, the concentration of oxygen may be lowered as the concentration of ethylene is increased. The actual safe operating ranges depend, along with the gas composition (reactants and balance gases), also on individual plant conditions such as temperature and pressure.

More particularly, the maximum oxygen concentration which may be used, i.e. the oxygen flammability limit, is reduced by the gas containing higher concentrations of ethylene and/or ethylene oxide, by a higher temperature and/or by a higher pressure employed, and it is increased by the gas containing higher concentrations of paraffins such as methane and/or ethane. In each individual plant a so-called flammability equation is used to determine the concentration of oxygen which may be used with any given concentration of e.g. ethylene. This flammability equation can be expressed graphically in a so-called flammability curve.

"GHSV" or Gas Hourly Space Velocity, is the unit volume of gas at standard temperature and pressure (0° C., 1 atm, i.e. 101.3 kPa) passing over one unit volume of packed catalyst per hour. Preferably, the process is carried out at a GHSV in the range of from 1500 to 10000. The reaction temperature is preferably in the range of from 180 to 325° C., and the reactor inlet pressure is preferably in the range of from 1000 to 3500 kPa.

The work rate w, which is the amount of ethylene oxide produced per unit volume of catalyst (kg per $m^3$, or gram per liter, etc.) per hour, is influenced by the temperature, the pressure and the gas velocity used. Preferably, the process of this invention is carried out at a work rate w in the range of from 25 to 400 kg ethylene oxide produced per $m^3$ of catalyst per hour, in particular 32 to 320 kg ethylene oxide produced per $m^3$ of catalyst per hour, for example 200 kg ethylene oxide produced per $m^3$ of catalyst per hour.

The value of the selectivity parameter S, expressed in mol % of the desired ethylene oxide formed relative to the total of ethylene converted at a given work rate w, will vary with the value of the actual work rate w.

The value of the activity parameter T, which is the operating temperature, expressed in ° C., needed to reach a given work rate w, will also vary with the value of w.

In a preferred embodiment of this invention, the reaction gas mixture contains ethylene at a concentration which represents an economically optimized balance between catalyst performance (expressed, at the given work rate w, by the selectivity S and by the activity parameter T) on the one hand and ethylene vent losses on the other, and oxygen at a concentration which complies with the safety-related flammability restrictions.

The optimal ethylene concentration, calculated on the total of the reaction mixture, which is used in the initial operation phase, depends on the plant, the catalyst, the reaction conditions and the work rate w chosen. Preferably, the ethylene concentration, calculated on the total of the reaction mixture, will be at most 50 mol %. More preferably, it will be in the range of from 2 to 45 mol %, in particular from 2 to 40 mol % of ethylene, the concentration usually used with air operated plants ranging from 2 to 15 mol % and the concentration usually used in oxygen operated plants ranging from 15 to 45 mol %, in particular 15 to 40 mol % of ethylene.

As used herein, the composition of the reaction mixture means is deemed to be the composition of the gas feed to the reactor, expressed as a fraction, e.g. in mol % or ppm by volume (ppmv), relative to the total gas feed.

In the further operation phase according to the present invention, the concentration of ethylene is increased preferably to a level of from 1.1 to 4 times the concentration of ethylene used in the initial operation phase. More particularly it will be raised by from 5 to 30 mol % of ethylene, preferably by from 10 to 20 mol %. Preferably, the concentration of ethylene is increased to at least 30 mol %, more preferably to at least 40 mol %, in particular to at least 50 mol %. Preferably, the concentration of ethylene is increased to at most 90 mol %, more preferably to at most 80 mol %, in particular to at most 70 mol %.

In the further operation phase the concentration of ethylene is raised when the cumulative ethylene oxide production exceeds 0.01 kT ethylene oxide per $m^3$ of catalyst, wherein "kT" means $10^6$ kg. Typically the concentration of ethylene is raised when the cumulative ethylene oxide production exceeds 0.1 kT ethylene oxide per $m^3$ of catalyst, more typically 0.3 kT ethylene oxide per $m^3$ of catalyst, preferably 0.5 kT ethylene oxide per $m^3$ of catalyst, more preferably 1 kT ethylene oxide per $m^3$ of catalyst, in particular 1.5 kT ethylene oxide per $m^3$ of catalyst. Frequently, the concentration of ethylene will be raised before the cumulative ethylene oxide production exceeds 50 kT ethylene oxide per $m^3$ of catalyst, more frequently before the cumulative ethylene oxide production exceeds 10 kT ethylene oxide per $m^3$ of catalyst.

The increase in the ethylene concentration may be one or more stepwise increases, it may also involve one or more gradual increases over a period of time, or a combination of stepwise and gradual increases.

In the process oxygen is preferably applied at "the corresponding optimal concentration of oxygen", by which is meant the concentration of oxygen which, under the temperature and pressure conditions employed and combined with the chosen concentration of ethylene, secures optimal performance while avoiding the flammability limit.

Generally, the concentration of oxygen applied in the initial operation phase will be within the broad range of from 6 to 12 mol % of the total gas feed.

Preferably, in the further operation phase according to the present invention, the concentration of oxygen used will be lowered to a level of 0.98 to 0.3 times the concentration of oxygen used in the initial operation phase, and more particularly it will be lowered by from 0.4 to 3.5 mol %, typically depending on the level by which the ethylene concentration is raised. Typically for any mol % absolute increase in ethylene concentration, the oxygen concentration may be decreased by from 0.02 to 0.15 mol % absolute, more typically from 0.05 to 0.1 mol % absolute, for example 0.08 mol % absolute. Typically for any % relative increase in the ethylene concentration, the relative decrease in the oxygen concentration may be from 0.05 to 0.8%, more typically from 0.15 to 0.5%, for example 0.22%. Preferably, the concentration of oxygen is decreased to at most 10 mol %, more preferably to at most 8 mol %. Preferably, the concentration of oxygen is decreased to at least 3 mol %, more preferably to at least 4 mol %. Generally, the change in the oxygen concentration, if any, may be co-current with the change in the ethylene concentration.

In addition to ethylene and oxygen, the reaction mixture of the process of this invention may contain one or more optional components, such as carbon dioxide, a gas phase moderator and balance inert gases.

Carbon dioxide is a by-product of the ethylene oxidation process. Since frequently unconverted ethylene is continuously recycled, and since concentrations of carbon dioxide in the reactor feed which are much in excess of 15 mol % will have an adverse effect on catalyst activity, accumulation of carbon dioxide will be avoided by and continuously removing carbon dioxide from the recycle gas. This may be done by venting and by continuous absorption of the formed carbon dioxide. Currently concentrations of carbon dioxide as low as 1 mol % are practical, and in future even lower concentrations may be reached. The process of the present invention is independent of the presence or absence of carbon dioxide in the reaction mixture.

A gas phase catalyst moderator may be added to the feed for increasing the selectively, suppressing the undesirable oxidation of ethylene and of ethylene oxide to carbon dioxide and water. Many organic compounds, especially organic halides but also amines, organometallic compounds and aromatic hydrocarbons are known to be effective in this respect. Organic halides are the preferred gas phase catalyst moderators and they are effective without suppressing the desired reaction when used in concentrations ranging from 0.1 to 25 ppmv, in particular from 0.3 to 20 ppmv of the total volume of the feed gas.

The optimal concentration of gas phase catalyst moderator may depend on plant conditions and on the type of catalyst used. Conventional catalysts have relatively flat selectivity curves for the moderator (i.e. their selectivity is almost invariant over a wide range of moderator concentrations), and this property does not change during prolonged operation of the catalyst. Therefore the concentration of the moderator can be more freely chosen and it can remain the same during the entire lifespan of the catalyst. By contrast the highly selective catalysts tend to exhibit relatively steep moderator selectivity curves (i.e. selectivity varies considerably with relatively small changes in moderator concentration, and exhibits a pronounced maximum at the most advantageous or optimum level of moderator). This moderator optimum, moreover, does tend to change during prolonged operation. Consequently, the moderator concentration may be optimized repeatedly during operation if the maximum achievable selectivity is to be maintained. In the initial operation phase the concentration of the organic halides is typically in the range of from 0.5 to 10 ppmv, preferably from 2 to 8 ppmv of the total volume of the feed gas. In the further operation phase the concentration of the organic halides is typically in the range of from 2 to 25 ppmv, preferably from 3 to 16 ppmv of the total volume of the feed gas.

Preferred organic halides are $C_1$ to $C_8$ chlorohydrocarbons or bromohydrocarbons. More preferably they are selected from the group of methyl chloride, ethyl chloride, ethylene dichloride, ethylene dibromide, vinyl chloride or a mixture thereof. Most preferred gas phase catalyst moderator are ethyl chloride and ethylene dichloride.

The balance inert gases usually present in the reaction feed comprise varying concentrations of nitrogen, argon, and added saturated hydrocarbon such as methane or ethane. Since unconverted ethylene is continuously recycled, and oxygen added, the accumulation of balance gases has to be avoided. The process of the present invention is independent of the amount of balance inert gases in the reaction mixture.

The efficiency of the ethylene oxidation reaction and catalyst is defined by selectivity S and activity T.

In both the initial operating phase and the further operation phase, the optimal ethylene concentration may be determined by successively measuring, at a fixed value of w, the performance in terms of S and T of progressively raised concentrations of ethylene, coupled with the corresponding safe concentrations of oxygen, until no further improvement can be reached.

The material of the support of the supported silver based catalysts can be selected from a wide range of conventional materials which are considered to be inert in the presence of the ethylene oxidation feeds, products and reaction conditions. Such conventional materials can be natural or artificial and they include the aluminum oxides, magnesia, zirconia, silica, silicon carbide, clays, pumice, zeolites and charcoal. Alpha alumina is the most preferred material to be used as the main ingredient of the porous support.

The support is porous and preferably has a surface area, as measured by the B.E.T. method, of less than 20 m$^2$/g and more in particular from 0.05 to 20 m$^2$/g. Preferably the B.E.T. surface area of the support is in the range of 0.1 to 10, more preferably from 0.1 to 3.0 m$^2$/g. The B.E.T. method of measuring the surface area has been described in detail by Brunauer, Emmet and Teller in *J. Am. Chem. Soc.* 60 (1938) 309–316.

A highly selective supported silver-based catalyst according to the present invention is one which, when operated fresh, exhibits at 260° C. a theoretical selectivity at zero work rate, $S_0$, of at least 6/7 or 85.7%. The value of $S_0$ for a given catalyst is found by operating the catalyst at 260° C. in a range of work rates w, resulting in a range of selectivity values S corresponding to the range of work rates w. These values S are then extrapolated back to the theoretical value of S at zero work rate, by the use of conventional curve-fitting algorithms, such as those provided with the MICROSOFT® Excel program.

The supported highly selective silver-based catalysts to be used in the present invention are rhenium containing catalysts. Such catalysts are known from EP-B-266015. Broadly, they contain a catalytically effective amount of silver, a promoting amount of rhenium or compound thereof, a promoting amount of at least one further metal or compound thereof and optionally a co-promoting amount of a rhenium co-promoter which can be selected from one or more of sulfur, phosphorus, boron, and compounds thereof, on a refractory support. More specifically the at least one further metal of these rhenium containing catalysts is/are selected from the group of alkali metals, alkaline earth metals, molybdenum, tungsten, chromium, titanium, hafnium, zirconium, vanadium, thallium, thorium, tantalum, niobium, gallium and germanium and mixtures thereof. Preferably the at least one further metal is/are selected from the alkali metals such as lithium, potassium, rubidium and cesium and/or from the alkaline earth metals such as calcium and barium. Most preferably it is lithium, potassium and/or cesium.

Preferred amounts of the components of these catalysts are, when calculated as the element on the total catalyst:

silver from 10 to 300 g/kg, rhenium from 0.01 to 15 mmol/kg, further metal or metals from 10 to 3000 mg/kg, and optional rhenium co-promoter from 0.1 to 10 mmol/kg.

The ethylene oxide produced may be recovered from the reaction mixture by using methods known in the art, for example by absorbing the ethylene oxide from a reactor outlet stream in water and optionally recovering the ethylene oxide from the aqueous solution by distillation. At least a portion of the aqueous solution containing the ethylene oxide may be applied in a subsequent process for converting the ethylene oxide into a 1,2-diol or a 1,2-diol ether.

The ethylene oxide produced in the present process, i.e. ethylene oxide, may be converted into 1,2-ethanediol or into a 1,2-ethanediol ether. The improved catalyst performance achieved by this invention leads to a more attractive process for the production of ethylene oxide and concurrently to a more attractive process which comprises producing ethylene oxide and the subsequent use of the obtained ethylene oxide in the manufacture of 1,2-ethanediol and/or a 1,2-ethanediol ether.

The conversion into 1,2-ethanediol or a 1,2-ethanediol ether may comprise, for example, reacting the ethylene oxide with water, suitably using an acidic or a basic catalyst. For example, for making predominantly 1,2-ethanediol and less 1,2-ethanediol ethers, the ethylene oxide may be reacted with a ten fold molar excess of water, in a liquid phase reaction in presence of an acid catalyst, e.g. 0.5–1.0% w sulfuric acid, based on the total reaction mixture, at 50–70° C. at 1 bar absolute, or in a gas phase reaction at 130–240° C. and 20–40 bar absolute, preferably in the absence of a catalyst. If the proportion of water is lowered the proportion of 1,2-ethanediol ethers in the reaction mixture is increased. The 1,2-ethanediol ethers thus produced may be the di-ether, tri-ether, tetra-ether and subsequent ethers. Alternative 1,2-ethanediol ethers may be prepared by converting the ethylene oxide with an alcohol, in particular a primary alcohol, such as methanol or ethanol, by replacing at least a portion of the water by the alcohol.

The 1,2-ethanediol and the 1,2-ethanediol ethers may be used in a large variety of industrial applications, for example in the fields of food, beverages, tobacco, cosmetics, thermoplastic polymers, curable resin systems, detergents, heat transfer systems, etc.

The following examples will illustrate the invention.

Part I: The Catalysts

Catalyst A was S-882, a commercial Shell catalyst of the High Selectivity type as defined in EP-B-266015, containing rhenium promoter and rhenium co-promoter and having a theoretical selectivity $S_0$ of 93% in the fresh state.

Comparative Catalyst B was S-860, a commercial Shell catalyst of the conventional type as defined in U.S. Pat. No. 5,380,697, not containing rhenium and rhenium co-promoter and having a theoretical selectivity $S_0$ of 85% in the fresh state.

The above values of $S_0$ were determined by collecting a range of selectivities S at multiple space velocities, each time at 30% ethylene, 8% oxygen, 5% carbon dioxide and 14 bar for both catalysts, the reaction temperature being 260° C. for Catalyst A and 235° C. for Catalyst B—and extrapolating back to infinite space velocity (i.e. zero work rate).

Fresh and aged Catalyst A and Comparative Catalyst B were tested. The aged catalyst A was taken from a commercial plant where it had been used for 21 months, having produced a total of 2400 Kg of ethylene oxide per liter of catalyst. The aged Comparative Catalyst B was taken from a commercial plant where it had been used for 34 months, having produced a total of 4500 Kg of ethylene oxide per liter of catalyst. Both aged catalysts were taken from the heart of the respective reactor tubes. They were analyzed and found to be free of contaminates.

Part II: The Catalyst Test Procedure

In each experiment, 1 to 5 grams of crushed catalyst (0.8–1.4 mm) were loaded into a micro-reactor consisting of a 3 mm internal diameter-stainless steel U-shaped tube. The U-shaped tube was immersed in a molten metal tin/bismuth bath (heat medium) and the ends were connected to a gas flow system. The weight of the catalyst and the inlet gas flow rate were adjusted to achieve a gas hourly space velocity of 3300 ml of gas per ml of catalyst per hour. The inlet gas pressure was 1600 kPa.

In each experiment, the effect on one fresh or aged catalyst of one of seven equally spaced concentrations of ethylene in the feed, ranging from 25 to 55 mol %, was tested under optimized further feed and temperature conditions. In the feed, the concentration of oxygen used in each experiment was the maximum allowed within the flammability limit and ranged from 9 to 6.5 mol %. The concentration of carbon dioxide was set to a typical level for each type of catalyst, i.e., 3.5% for the fresh highly selective catalyst, and 5.0% for the aged highly selective catalyst and for the conventional catalysts. The concentration of ethyl chloride was optimized over the range of 2.0–4.0 ppmv for the fresh highly selective catalyst, optimized over the range of 3.0–7.0 ppmv for the aged highly selective catalyst, and set at 2.5 ppmv for the fresh and aged conventional catalysts. Nitrogen ballast comprised the remainder of the bulk feed mixture. The temperature in each experiment was adjusted, by raising it gradually, to achieve a constant work rate w (mg of ethylene oxide produced per ml of catalyst per hour). In accordance with typical commercial practice, the constant work rate w was 200 kg/m$^3$/hr for the fresh and aged S-882 catalyst and for the fresh S-860 catalyst, and 160 kg/m$^3$/hr for the aged S-860 catalyst.

Part III: The Results

Figure 2:
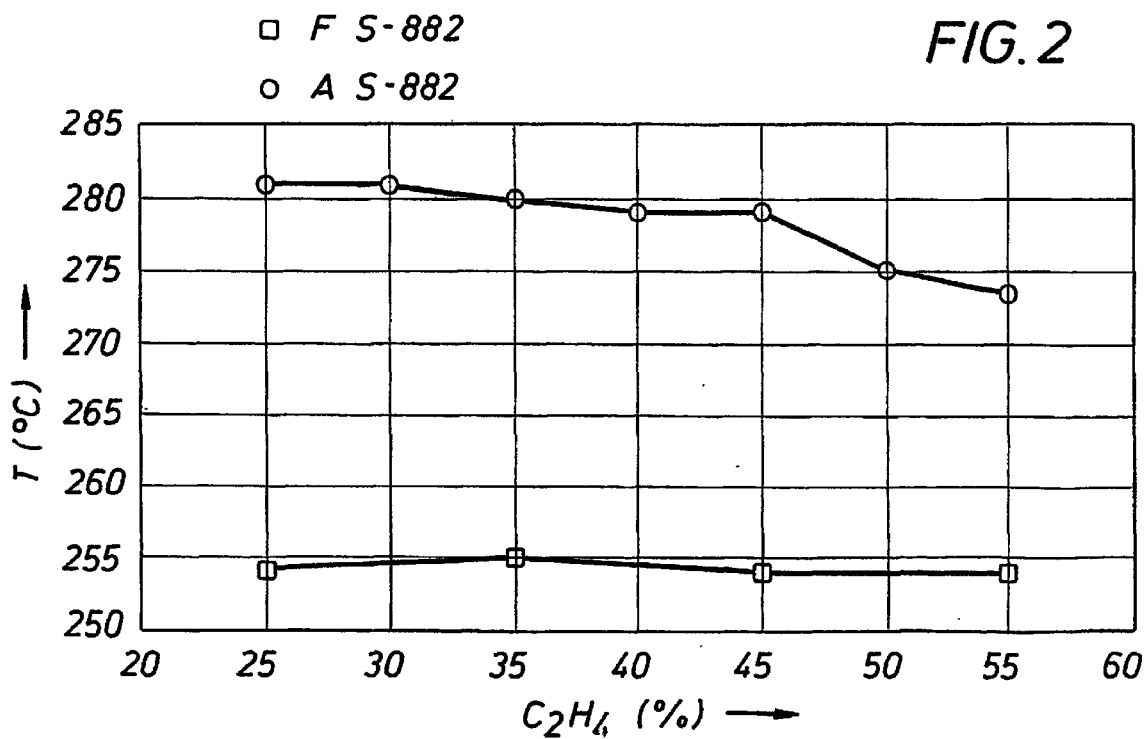
FIG. 2 shows for a fresh high selectivity catalyst ("F S-882") and an aged high selectivity catalyst ("A S-882") the activity ("T") versus the ethylene concentration ("$C_2H_4$, %") in the gas feed.
Figure 3:
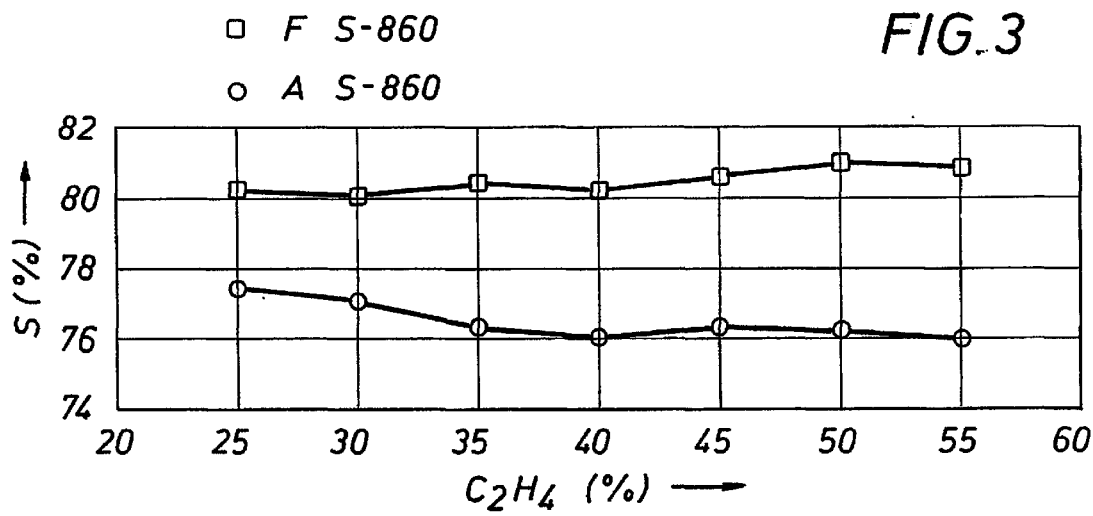
FIG. 3 shows for a fresh conventional catalyst ("F S-860") and an aged conventional catalyst ("A S-860") the selectivity ("S") versus the ethylene concentration ("$C_2H_4$, %") in the gas feed.
Figure 4:
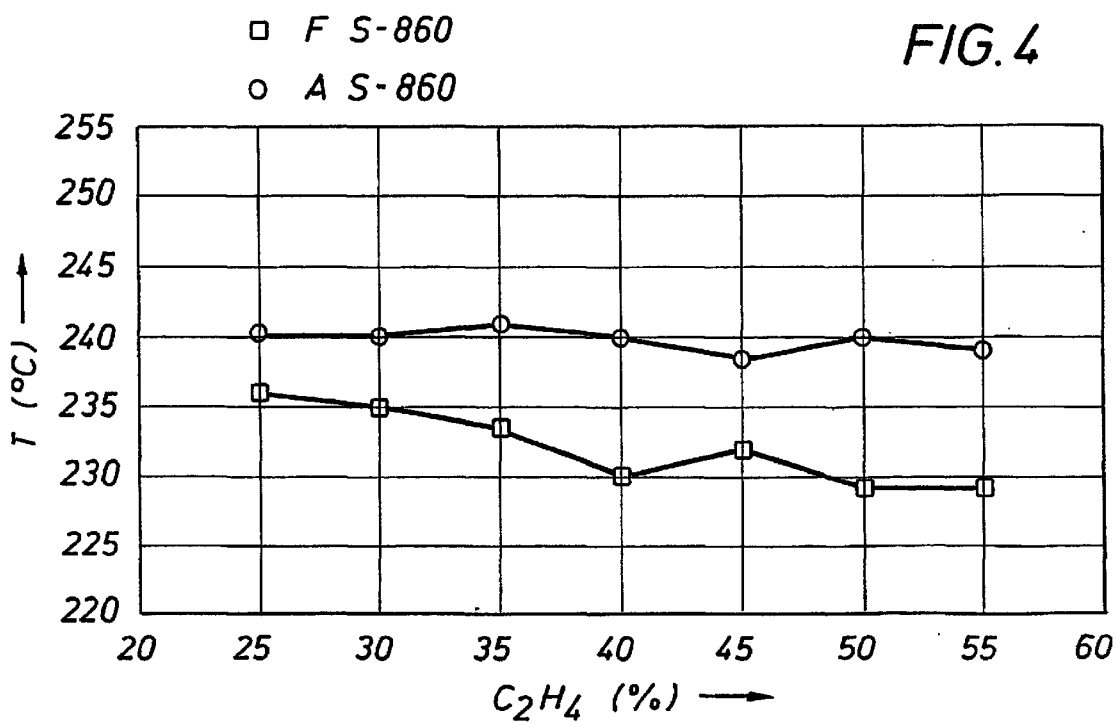
FIG. 4 shows for a fresh conventional catalyst ("F S-860") and an aged conventional catalyst ("A S-860") the activity ("T") versus the percent ethylene concentration ("$C_2H_4$, %") in the gas feed.

The results are given in the following Table I (EO denotes ethylene oxide) and in FIGS. 1 to 4. In all the Figures, the percentage of oxygen was adjusted to conform with flammability.

TABLE I

| Example | Catalyst | $O_2$, mol % in feed | $C_2H_4$, mol % in feed | S (% EO) | T (° C.) |
|---|---|---|---|---|---|
| Comp. 1 | S-882, FRESH | 9.1 | 25 | 87.5 | 254 |
| Comp. 2 | S-882, FRESH | 8.2 | 35 | 87.6 | 255 |
| Comp. 3 | S-882, FRESH | 7.4 | 45 | 87.1 | 254 |
| Comp. 4 | S-882, FRESH | 6.6 | 55 | 87.2 | 254 |
| 5 | S-882, AGED | 9.0 | 25 | 80.7 | 281 |
| 6 | S-882, AGED | 8.6 | 30 | 81.4 | 281 |
| 7 | S-882, AGED | 8.2 | 35 | 82.8 | 280 |
| 8 | S-882, AGED | 7.8 | 40 | 82.9 | 279 |
| 9 | S-882, AGED | 7.4 | 45 | 83.2 | 279 |
| 10 | S-882, AGED | 7.0 | 50 | 83.2 | 275 |
| 11 | S-882, AGED | 6.6 | 55 | 83.7 | 274 |
| Comp. 12 | S-860, FRESH | 9.1 | 25 | 80.2 | 236 |
| Comp. 13 | S-860, FRESH | 8.7 | 30 | 80.1 | 235 |
| Comp. 14 | S-860, FRESH | 8.2 | 35 | 80.3 | 233 |
| Comp. 15 | S-860, FRESH | 7.8 | 40 | 80.1 | 230 |
| Comp. 16 | S-860, FRESH | 7.4 | 45 | 80.6 | 232 |
| Comp. 17 | S-860, FRESH | 7.0 | 50 | 80.9 | 229 |
| Comp. 18 | S-860, FRESH | 6.6 | 55 | 80.8 | 229 |
| Comp. 19 | S-860, AGED | 9.1 | 25 | 77.4 | 240 |
| Comp. 20 | S-860, AGED | 8.7 | 30 | 76.9 | 240 |
| Comp. 21 | S-860, AGED | 8.2 | 35 | 76.2 | 241 |
| Comp. 22 | S-860, AGED | 7.8 | 40 | 76.0 | 240 |
| Comp. 23 | S-860, AGED | 7.4 | 45 | 76.3 | 238 |
| Comp. 24 | S-860, AGED | 7.0 | 50 | 76.2 | 240 |
| Comp. 25 | S-869, AGED | 6.6 | 55 | 75.9 | 239 |

From these results it emerges that in particular the aged S-882 catalyst is distinguished over the fresh S-882 and S-860 and the aged S-860 in that its performance (selectivity as well as activity) is clearly improved when the concentration of ethylene in the feed is raised from 25 to 55 mol %. With the fresh highly selective catalysts the selectivity of the reaction towards ethylene oxide is not influenced substantially when a higher concentration of ethylene is combined with a lower (i.e. safe) concentration of oxygen, while with the aged highly selective catalysts the selectivity under these conditions is substantially improved. Differences of activity performance under conditions of raised ethylene concentration and lowered oxygen concentration between fresh and aged highly selective catalysts are in the same direction but less pronounced. By contrast to the highly selective catalysts it has been found that aged and fresh traditional ethylene oxidation catalysts do not exhibit this clear difference in their reaction to the composition of the feed gas mixture. Thus, by raising the ethylene content of the reaction gas mixture, yet simultaneously reducing the oxygen content to remain below the flammability limit, both selectivity and activity of the aged high selectivity catalyst are improved significantly.

What is claimed is:

1. A process for the vapor phase oxidation of ethylene to ethylene oxide, which process comprises reacting a reaction mixture comprising ethylene and oxygen in the presence of a supported highly selective silver-based catalyst comprising a catalytically effective amount of silver, a promoting amount of rhenium or compound thereof, and a promoting amount of at least one further metal or compound thereof, by:

operating at an initial operation phase wherein fresh catalyst is used, and operating at a further operation phase when a cumulative ethylene oxide production exceeds 0.01 kT ethylene oxide per m$^3$ of catalyst, wherein in said further operation phase the concentration of ethylene in the reaction mixture is increased.

2. A process as claimed in claim 1, wherein in the further operation phase the concentration of ethylene is raised when the cumulative ethylene oxide production exceeds 0.3 kT ethylene oxide per m$^3$ of catalyst.

3. A process as claimed in claim 2, wherein in the further operation phase the concentration of ethylene is raised when the cumulative ethylene oxide production exceeds 0.5 kT ethylene oxide per m$^3$ of catalyst.

4. A process as claimed in claim 3, wherein in the further operation phase the concentration of ethylene is raised when the cumulative ethylene oxide production exceeds 1 kT ethylene oxide per m$^3$ of catalyst.

5. A process as claimed in claim 1, wherein the concentration of ethylene is increased to from 1.1 to 4 times the concentration of ethylene used in the initial operation phase.

6. A process as claimed in claim 5, wherein the concentration of oxygen used is lowered to from 0.98 to 0.3 times the concentration of oxygen used in the initial operation phase.

7. A process according to claim 1, wherein the supported highly selective silver based catalyst comprises a catalytically effective amount of silver, a promoting amount of rhenium or compound thereof, a promoting amount of at least one further metal or compound thereof, and a co-promoting amount of a rhenium co-promoter selected from one or more of sulfur, phosphorus, boron, and compounds thereof.

8. A process according to claim 7, wherein the at least one further metal is selected from alkali metals, alkaline earth metals, molybdenum, tungsten, chromium, titanium, hafnium, zirconium, vanadium, thallium, thorium, tantalum, niobium, gallium, germanium and mixtures thereof.

9. A process according to claim 8, wherein the at least one further metal comprises lithium, potassium and/or cesium.

10. A process according to claim 8, wherein, calculated as the element on the total catalyst, the amount of silver is in the range of from 10 to 300 g/kg, the amount of rhenium is in the range of from 0.01 to 15 mmol/kg, the amount of further metal or metals is in the range of from 10 to 3000 mg/kg, and the amount of optional rhenium co-promoter is in the range of from 0.1 to 10 mmol/kg.

11. A process according to claim 1, wherein the support is porous and its surface area is in the range of from 0.05 to 20 $m^2/g$.

12. A process according to claim 11, wherein the material of the support is mainly alpha alumina.

13. A process according to claim 1, wherein the gas phase moderator is 0.3 –25 ppmv of an organic halide.

14. A process according to claim 13, wherein the organic halide is a $C_1$ to $C_8$ chlorohydrocarbon or bromohydrocarbon.

15. A process according to claim 14, wherein the organic halide is selected from methyl chloride, ethyl chloride, ethylene dichloride, ethylene dibromide, vinyl chloride and mixtures thereof.

16. A process according to claim 1, wherein in the further operation phase the composition of the reaction mixture is changed to contain from 5 to 30 mol % more of ethylene than the concentration of ethylene used in the initial operation phase.

17. A method of making 1,2-ethanediol or a corresponding 1,2-ethanediol ether comprising producing ethylene oxide by vapor phase oxidation of ethylene, and converting the ethylene oxide into the 1,2-ethanediol or the 1,2-ethanediol ether, wherein the vapor phase oxidation of ethylene to ethylene oxide comprises reacting a reaction mixture comprising ethylene and oxygen in the presence of a supported highly selective silver-based catalyst comprising a catalytically effective amount of silver, a promoting amount of rhenium or compound thereof, and a promoting amount of at least one further metal or compound thereof, by:

operating at an initial operation phase wherein fresh catalyst is used, and operating at a further operation phase when a cumulative ethylene oxide production exceeds 0.01 kT ethylene oxide per $m^3$ of catalyst, wherein in said further operation phase the concentration of ethylene in the reaction mixture is increased.

* * * * *